United States Patent
Richard et al.

(10) Patent No.: US 10,421,706 B2
(45) Date of Patent: Sep. 24, 2019

(54) METHOD FOR ESTERIFICATION OF A DIOL USING A REACTIVE DISTILLATION

(71) Applicants: IFP Energies Nouvelles, Rueil-Malmaison (FR); Compagnie Generale des Etablissements Michelin, Clermont-Ferrand (FR)

(72) Inventors: Romain Richard, St. Quentin Fallavier (FR); Damien Leinekugel Le Cocq, Lyons (FR); Marc Jacquin, Lyons (FR); Margarita Dorato, Clermont-Ferrand (FR); Nuno Pacheco, Clermont-Ferrand (FR); Claire Rannoux, Clermont-Ferrand (FR)

(73) Assignees: IFP Energies Nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 15/551,754
(22) PCT Filed: Feb. 17, 2016
(86) PCT No.: PCT/EP2016/053300
§ 371 (c)(1),
(2) Date: Aug. 17, 2017
(87) PCT Pub. No.: WO2016/131845
PCT Pub. Date: Aug. 25, 2016

(65) Prior Publication Data
US 2018/0022682 A1    Jan. 25, 2018

(30) Foreign Application Priority Data
Feb. 18, 2015 (FR) ...................... 15 51354

(51) Int. Cl.
*C07C 67/08* (2006.01)
*C07C 1/213* (2006.01)
(Continued)

(52) U.S. Cl.
CPC .............. *C07C 67/08* (2013.01); *C07C 1/213* (2013.01); *C07C 67/54* (2013.01); *C07C 67/58* (2013.01);
(Continued)

(58) Field of Classification Search
None
See application file for complete search history.

(56) References Cited

U.S. PATENT DOCUMENTS 2,224,912 A * 12/1940 Hill .................. C07C 1/213
560/112
3,647,903 A   3/1972 Maurin
(Continued)

FOREIGN PATENT DOCUMENTS

WO    2011117707 A1    9/2011

OTHER PUBLICATIONS

Schneipp ("Continuous Process for Acetylation of 2,3-Butylene Glycol" Industrial and Engineering Chemistry, vol. 37, 1945, p. 872-877) (Year: 1945).*

(Continued)

*Primary Examiner* — Amy C Bonaparte
(74) *Attorney, Agent, or Firm* — Millen, White, Zelano and Branigan, P.C.

(57) ABSTRACT

The invention relates to a conversion method that is fed with a diol feedstock that comprises at least 90% by weight of diol and a carboxylic acid feedstock that comprises at least 80% by weight of carboxylic acid. The method comprising at least:
An esterification step which is fed with at least the diol feedstock and at least the carboxylic acid feedstock, wherein the carboxylic acid/diol molar ratio at the inlet of the esterification step is between 2 and 6, the esterification step comprises at least one reactive distillation column that has a mixed reaction/separation zone located between two separation zones; and
A water elimination step that is fed with distillate from the esterification step that comprises water and producing at least one water effluent.

16 Claims, 2 Drawing Sheets

(51) Int. Cl.
*C07C 67/54* (2006.01)
*C07C 67/58* (2006.01)
*C07C 69/08* (2006.01)
*C07C 69/16* (2006.01)
*C07C 69/28* (2006.01)

(52) U.S. Cl.
CPC .............. *C07C 69/08* (2013.01); *C07C 69/16* (2013.01); *C07C 69/28* (2013.01); *Y02P 20/127* (2015.11)

(56) References Cited

U.S. PATENT DOCUMENTS

2003/0109742 A1* 6/2003 Wu .................. C07C 67/08
560/103
2013/0131376 A1 5/2013 Marenco

OTHER PUBLICATIONS

"Esterification" chapter of Kirk-Othmer Encyclopedia of Chemical Technology, vol. 10, published Dec. 4, 2000, p. 471-496, downloaded from https://onlinelibrary.wiley.com/doi/10.1002/0471238961.0519200501191201.a01 on Oct. 31, 2018 (Year: 2000).*
Lothmer, Donald et al.; Esterification of 2,3-Butylene Glycol with Acetic Acid; Ind. Eng. Chem., 1945, 37 (9), pp. 900-905 DOI: 10.1021/ie50429a028 Publication Date: Sep. 1945.
International Search Report PCT/EP2016/053300 dated Feb. 5, 2016.

* cited by examiner

METHOD FOR ESTERIFICATION OF A DIOL USING A REACTIVE DISTILLATION

TECHNICAL FIELD OF THE INVENTION

The invention relates to the production of diesters and diolefins from diols. The invention is particularly well suited to the production of 1,3-butadiene from 1,4-butanediol, 1,3-butanediol and 2,3-butanediol.

PRIOR ART

Today, 95% of the production of 1,3-butadiene is ensured by the steam-cracking of hydrocarbons and the subsequent extraction of diolefins within a $C_4$ distillation fraction by extractive distillation methods.

The changes in price of raw materials lead to operating the steam-cracking units with feedstocks that are increasingly lighter because they are less expensive, bringing about the reduction in production of the $C_4$ fraction and consequently of 1,3-butadiene.

Other methods make it possible to produce butadiene on the industrial scale. It is possible to cite the methods for dehydrogenation of butenes and butanes, which are based on a $C_4$ hydrocarbon resource. It is also possible to mention the Lebedev method, which makes it possible to obtain 1,3-butadiene from ethanol.

Another method for producing 1,3-butadiene, carried out on a pilot scale in 1945 in the USA, is described in, for example, the patents FR 859902, U.S. Pat. No. 2,383,205, 2,372,221, and in *Industrial & Engineering Chemistry*, 37 (9), 1945, pp. 865 to 908. This method consists of three main steps:
  The fermentation of sugar into 2,3-butanediol;
  The esterification of 2,3-butanediol by a carboxylic acid to form the corresponding diester;
  The pyrolysis of diester for producing 1,3-butadiene and carboxylic acid, with the latter being recycled into the esterification step.

This method is particularly advantageous because the step for pyrolysis of diester can be carried out with very good yields (typically more than 80 mol %), and the 1,3-butadiene that is obtained is of high purity (typically more than 99% by weight), which is crucial for its use in various applications (fine chemistry, elastomer).

Furthermore, various diols can be obtained by fermentation. In particular, the production of 2,3-butanediol from sugar can be carried out in the laboratory stage with *Klebsiella pneumoniae* with excellent performances, at a final concentration of 2,3-butanediol in the fermentation must of 160 $g \cdot L^{-1}$. *Klebsiella oxytoca* has also been used in fermentations in the pilot stage. Nevertheless, *Klebsiella* is involved in serious pulmonary pathologies, which makes its use very problematic for the production of 2,3-butanediol.

Other non-pathogenic microorganisms make it possible to obtain $C_4$ diols. For example, the patent WO 12058508 describes the production of ethanol and 2,3-butanediol by fermentation of synthesis gas. The patent WO 10141780 describes the production of 1,4-butanediol by fermentation of sugar.

The step for esterification of 2,3-butanediol by acetic acid is described in the articles "Esterification of 2,3-Butylene Glycol with Acetic Acid" and "Continuous Process for Acetylation of 2,3-Butylene Glycol" of Industrial and Engineering Chemistry, Vol. 37, No. 9, pp. 900-905 and pp. 872-877 respectively.

This step is critical during the process because the diester that is produced is to be of high purity, i.e., to not contain diol monoester and diol, so as to obtain good butadiene production yields in the pyrolysis step. Furthermore, the diester yield in the esterification step is to be maximized so as not to penalize the overall yield of the method.

In the method of the prior art, the step for esterification of 2,3-butanediol is carried out by reactive distillation, with a homogeneous catalyst (sulfuric acid). The diol is introduced onto an intermediate plate located in the upper part of the distillation column, and the acetic acid is introduced in the reboiler of the distillation column. The water that is produced is drawn off at the top with a portion of the acetic acid that is introduced in excess, and the diester that is produced is drawn off at the bottom. The homogeneous catalyst is introduced with the diol and recovered at the bottom with the diester. Nevertheless, the embodiment of the prior art exhibits numerous drawbacks.

Actually, the boiling point of the diester is 204° C. at atmospheric pressure. A reactive distillation column that operates at atmospheric pressure producing a water-acetic acid mixture at the top and a pure diester at the bottom would therefore have a thermal profile ranging from 100-110° C. at the top to 204° C. at the bottom. However, beyond a temperature of 150° C., the presence of the homogeneous catalyst gives rise to secondary reactions for degradation of 2,3-butanediol, in particular with methyl ethyl ketone (MEK). These secondary reactions indirectly induce a loss of yield of butadiene that it is necessary to avoid at all costs. To minimize these degradation reactions, the approach adopted in the prior art consists in introducing a large excess of acetic acid into the reboiler of the distillation column—thus reducing the bubble temperature of the acetic acid/diester mixture that is drawn off at the bottom—and therefore the entire thermal profile in the column.

A first drawback of the approach adopted in the prior art is that the acetic acid is introduced with a large excess in relation to diol, greater than the excess that would be necessary to produce a diester of sufficient purity for the pyrolysis step. The introduction of this large excess of acetic acid induces an oversizing of the equipment, and an increase in the energy consumption to separate the water that is produced from the acetic acid that is not consumed.

A second drawback of the approach adopted in the prior art is that the acetic acid/diester/homogeneous catalyst mixture that is drawn off at the bottom is to be separated before sending the diester to the pyrolysis step. This separation is carried out thanks to a first distillation under a forced vacuum to minimize the operating temperature, and then a second distillation at atmospheric pressure. The first vacuum distillation column makes it possible to recover, at the bottom, the homogeneous catalyst that is recycled to the reactive distillation column and, at the top, an acetic acid/diester mixture. The latter is separated in the second distillation column at atmospheric pressure, producing acetic acid at the top and diester at the bottom. Acetic acid is recycled in the reactive distillation column, and the diester is sent to the pyrolysis step. Overall, these separation operations are costly both from an investment standpoint (vacuum distillation column) as well as an operating cost standpoint (vacuum, total evaporation of the acetic acid/diester mixture, . . . ).

In addition, MEK, unavoidably produced by the degradation reaction, is recovered in the effluent that is drawn off at the top of the reactive distillation column with the water that is produced and the acetic acid that is introduced in excess. This water and this acetic acid should then be separated: water is eliminated from the method, and acetic acid is recycled into the esterification step. It is well known to one skilled in the art that the separation of water and acetic acid cannot be carried out by simple distillation. Actually, the presence of a narrowing in the liquid-vapor equilibrium curves does not make it possible to eliminate in an effective manner the entire acetic acid within an aqueous effluent. The water and the acetic acid are therefore separated by carrying out a heterogeneous azeotropic distillation, which uses a driver. The driver forms an azeotrope with water, which is drawn off at the top of two distillation columns: one that produces a residue consisting of water and the other that produces a residue consisting of acetic acid. The distillate from these two distillation columns is condensed in a decanter tank. Because of the non-miscibility between the driver and water, a phase separation takes place: a water-rich phase that is sent back as reflux into the column that produces the residue consisting of water and a driver-rich phase that is sent back as reflux into the column that produces the residue consisting of acetic acid are obtained. The acetic acid that could have been entrained in the distillates is preferably shared in the driver-rich phase and is therefore preferably sent back into the column that produces the residue consisting of acetic acid. The presence of MEK in this heterogeneous azeotropic distillation is extremely problematic. Actually, since MEK is more volatile than the water/driver azeotrope, it starts at the top of the distillation columns and accumulates in the decanter tank. Beyond a certain content, MEK makes the water/acetic acid/driver mixture one-phase: water and acetic acid can then no longer be separated. To resolve this problem, the approach adopted in the prior art consists in distilling the driver-rich phase to eliminate MEK, before sending it back to the distillation column that produces a residue consisting of acetic acid. Nevertheless, finding a high-performing driver for the water/ acetic acid separation and that is easily separable from MEK is not obvious. The operation for separation of water and acetic acid is therefore made more complex because of the presence of MEK.

Finally, a last problem of the approach adopted in the prior art is associated with the corrosion of equipment. Acetic acid is not very corrosive, except at high concentrations and high temperatures that are found at the bottom of the column. These corrosion problems are exacerbated by the presence of a mineral homogeneous catalyst such as the sulfuric acid that was used in the prior art.

It should be noted that the problems set forth above are not specific to the case of 2,3-butanediol. For example, if it was desired to carry out the esterification of 1,4-butanediol or 1,3-butanediol with acetic acid, the thermal profiles within the reactive distillation column would be similar to those observed in the case of the esterification of 2,3-butanediol, with the position of the oxidized groups on the carbon-containing skeleton having little impact on the boiling points. Furthermore, the presence of secondary reactions activated by the temperature in the presence of the homogeneous catalyst are inevitable regardless of the diol, even if the nature of the by-products varies. Actually, with 1,4-butanediol or 1,3-butanediol, the by-product that is formed for the most part would not be MEK but tetrahydrofuran. The latter is as problematic as MEK within the heterogeneous azeotropic distillation section that separates the water that is produced from the acetic acid that is introduced in excess.

This invention makes it possible to resolve one or more problems of the prior art. Actually, the applicant discovered an implementation of the reactive distillation of a diol with a carboxylic acid that makes it possible to produce a diester of high purity, while minimizing excess carboxylic acid and the degradation reactions.

OBJECT AND ADVANTAGE OF THE INVENTION

The invention relates to a conversion method fed with a diol feedstock that comprises at least 90% by weight of diol and a carboxylic acid feedstock that comprises at least 80% by weight of carboxylic acid, with said method comprising at least:

An esterification step, fed with at least said diol feedstock and at least said carboxylic acid feedstock, with the feed flow rates being adjusted in such a way that the carboxylic acid/diol molar ratio at the inlet of said esterification step is between 2 and 6, with said esterification step comprising at least one reactive distillation column operated at a temperature of between 40 and 280° C., at a pressure of between 0.01 and 0.5 MPa, with a molar reflux rate of between 0.5 and 10, and a molar reboil rate of between 0.5 and 10, consisting of a mixed reaction/separation zone located between two separation zones, with each of said separation zones having an effectiveness of at least two theoretical stages, said mixed zone comprising an acid heterogeneous catalyst, said esterification step producing at least one distillate that comprises water and a diol-diester residue;

A water elimination step that is fed with said distillate that comprises water and that produces at least one water effluent.

One advantage of the invention is to be able to minimize the operating costs and investments associated with the diol-diester esterification step. Another advantage of the invention is to be able to minimize the degradation reactions of the diol feedstock, and therefore to improve the yield of the esterification method. The use of a heterogeneous catalyst instead of a homogeneous catalyst also makes it possible to resolve the problem of effluent/catalyst separation.

DETAILED DESCRIPTION OF THE INVENTION

Feedstock

In accordance with the invention, the conversion method is fed with a diol feedstock that comprises at least 90% by weight of diol. Said diol feedstock can also comprise water. In particular, said diol feedstock can stem from a method for treating effluents with a fermentation of sugars or synthesis gas or hydrogenolysis of a compound that is obtained from renewable resources such as sorbitol, for example, and producing a diol.

Said diol is advantageously selected from among butanediols, pentanediols, and hexanediols, taken by themselves or in a mixture, preferably butanediols. In a preferred manner, said diol is selected from among 2,3-butanediol, 1,3-butanediol, and 1,4-butanediol; in a very preferred manner, said diol is 2,3-butanediol.

In accordance with the invention, the conversion method is also fed with a carboxylic acid feedstock that comprises at least 80% by weight of carboxylic acid, and preferably more than 95% by weight of carboxylic acid. Said carboxylic acid feedstock can comprise water, preferably less than 5% by weight of water, in a preferred manner less than 1% by weight of water, and in a very preferred manner less than 0.1% by weight of water. Said carboxylic acid feedstock can comprise organic impurities.

Said carboxylic acid feedstock advantageously comprises the liquid pyrolysis effluent that is obtained from the pyrolysis step when the former is implemented.

Said carboxylic acid feedstock advantageously comprises the carboxylic acid residue that is obtained from the water elimination step when the former is used in a heterogeneous azeotropic distillation that is decoupled from the azeotropic distillation step.

Said carboxylic acid is advantageously selected from among the aliphatic carboxylic acids. In a preferred manner, the carboxylic acid is selected from among formic acid, acetic acid, propanoic acid, and butanoic acid. In a preferred manner, carboxylic acid is acetic acid.

In a preferred arrangement of the invention, the conversion method can also be fed with a carboxylic anhydride feedstock. This carboxylic anhydride feedstock does not contain water by definition, but can contain the corresponding carboxylic acid. The carboxylic anhydride that is used in the conversion method according to the invention is the carboxylic anhydride that corresponds to the carboxylic acid of said carboxylic acid feedstock. In a preferred manner, the acetic anhydride is acetic anhydride [sic].

The acetic anhydride feedstock is introduced into the method in such a way as to compensate, partially or totally, the losses of carboxylic acid in the pyrolysis step. The flow rate of the carboxylic anhydride feedstock is therefore very low with respect to the flow rate of the carboxylic acid feedstock.

Esterification Step

In accordance with the invention, the esterification method comprises at least one esterification step, fed with said diol feedstock and with said carboxylic acid feedstock, with the feed flow rates being adjusted in such a way that the carboxylic acid/diol molar ratio at the inlet of the esterification step is between 2 and 6, preferably between 2 and 4, and in a very preferred manner between 2 and 3.5. In a preferred arrangement of the invention, the esterification method is also fed with the carboxylic anhydride feedstock.

Said esterification step produces at least one distillate that comprises water and a diol-diester residue. It comprises at least one reactive distillation column that is operated at a pressure of between 0.01 and 0.5 MPa, and in a preferred manner at atmospheric pressure and at a temperature of between 40° C. and 280° C., with said reactive distillation column comprising a mixed reaction/separation zone located between two separation zones.

Said diol feedstock, optionally pre-esterified, is introduced into said reactive distillation column in an intermediate stage, preferably between the mixed zone and the separation zone located above the mixed zone. At least one fraction of said carboxylic acid feedstock is introduced into said reactive distillation column in one or more intermediate stages located below the stage for injection of the diol feedstock. In a preferred manner, said fraction of said carboxylic acid feedstock is introduced into the reactive distillation column in a single intermediate stage, located between the mixed zone and the separation zone located below. In a preferred arrangement of the invention, the carboxylic anhydride feedstock is introduced into the reactive distillation column with the carboxylic acid feedstock or else in a single intermediate stage, below the stage for injection of the carboxylic acid feedstock.

Intermediate stage is defined as a stage of the reactive distillation column that is neither the reboiler nor the condenser. Above or upper is defined as the direction of the condenser. Below or lower is defined as the direction of the reboiler.

In accordance with the invention, the molar reflux rate (equal to the reflux molar flow rate of the condenser toward the top of the column divided by the distillate molar flow rate) is between 0.5 and 10, in a preferred manner between 0.5 and 4, and in a very preferred manner between 1 and 2. In accordance with the invention, the molar reboil rate (equal to the reflux molar flow rate of the reboiler toward the bottom of the column divided by the molar residue flow rate) is between 0.5 and 10, in a preferred manner between 4 and 10, and in a very preferred manner between 5 and 6.

Each of said separation zones comprises internals that are known to one skilled in the art, such as plates, random packings or structured packings, or a combination of these types of internals, with said internals or said combination having overall an effectiveness of separation for each of said separation zones of at least two theoretical stages, preferably between two and ten theoretical stages, and in a preferred manner between two and four theoretical stages, in such a way as to ensure minimal yield and purity of the diol diester that is produced.

Said mixed zone comprises an acid heterogeneous catalyst. In a first particular arrangement, said mixed zone consists of plates and catalytic sections, which are located outside of the distillation column, with each catalytic section being connected to the plates of said mixed zone by means of a liquid draw-off on a plate of said mixed zone, with reinjection into the lower plate after passage into said catalytic section. Said mixed zone advantageously comprises at most 20, preferably at most 15, catalytic sections.

In a second particular arrangement, said mixed zone consists of internals that hold said catalyst. Said catalyst is then held in said mixed zone by the means that are known to one skilled in the art. In a non-limiting manner, the heterogeneous catalyst can be held between the plates of a structured packing, be imprisoned in metal grids deposited on the distillation plates, be imprisoned in a fabric shaped in such a way as to serve as a packing and to establish the transfer between the gas phase and the liquid phase, or else in a device for particular distribution of liquid and vapor phases as described in the patent FR 2,737,131. In a preferred manner, said mixed zone uses the device for particular distribution of the liquid and vapor phases as described in the patent FR 2,737,131. This device is preferred because it generates a smaller loss of feedstock within the column, with the gas phase being short-circuited by the catalyst zone. This device therefore makes it possible to maintain lower pressure at the bottom of the column and therefore a lower temperature. When a device for particular distribution of liquid and vapor phases as described in the patent FR 2,737,131 is used to hold the heterogeneous catalyst in the column, the mixed zone consists of alternating reaction sections and separation sections. In an advantageous manner, said mixed zone comprises, according to this embodiment, at most 20, preferably at most 15, reaction sections.

The dwell time of the liquid phase in each catalytic section according to the first particular arrangement, or in each reaction section in the second particular arrangement, is advantageously between 5 and 30 minutes, in a preferred manner between 15 and 25 minutes. In addition, the surface velocity of the liquid phase within the fixed catalyst bed is advantageously between 0.05 and 0.5 cm/s, and in a preferred manner between 0.1 and 0.3 cm/s.

Said heterogeneous acid catalyst is, in a non-limiting manner, an ion-exchange acid resin (such as Amberlyst, Amberlite, Dowex, and in particular an Amberlyst 35, an Amberlyst 36, or an Amberlyst 70), a mixed oxide ($ZrO_2$, SnO) or an acid zeolite (H-MOR, H-MFI, H-FAU, and H-BEA). In a preferred manner, said heterogeneous acid catalyst is stable at a temperature that is higher than 130° C., in a preferred manner higher than 150° C., and in a very preferred manner higher than 170° C.

The dwell time in said reactive distillation column, defined as the volume of the reactive distillation divided by the volumetric flow rate of said diol feedstock and said carboxylic acid feedstock, is advantageously between 0.5 h and 10 h, preferably between 0.5 h and 5 h, and in a preferred manner between 1 h and 2 h.

In a preferred manner, the MMH (mol per mol per hour, corresponding to the diol molar flow rate in the diol feedstock divided by the number of moles of catalyst present within said mixed zone) is between 0.05 and 25 $h^{-1}$, preferably between 0.15 and 20 $h^{-1}$.

In a preferred arrangement, said esterification step also comprises a pre-esterification section that is fed with said diol feedstock and a fraction of said carboxylic acid feedstock and that produces a pre-esterified diol feedstock consisting of diol that is not converted, diol monoester, diol diester, carboxylic acid that is not converted, and water, used in a fixed bed in the presence of a heterogeneous acid catalyst that can be identical to or different from the one that is used in the mixed zone of the esterification step. Said pre-esterification section is operated at a pressure of between 0.01 and 0.5 MPa, and in a preferred manner at atmospheric pressure, and at a temperature of between 80° C. and 170° C., and in a preferred manner between 100° C. and 140° C.

In a preferred manner, the MMH (corresponding to the diol molar flow rate in the diol feedstock divided by the number of moles of catalyst present within said pre-esterification step) is between 0.05 and 25 $h^{-1}$, preferably between 0.15 and $20^{-1}$.

The objective of the pre-esterification section is to convert all or part of the diol encompassed in said diol feedstock at least into monoester. This section has a particularly advantageous effect when the reaction for conversion of diol into monoester is slow in relation to the reaction for conversion of monoester into diester. The carboxylic acid feedstock fraction that feeds said pre-esterification section is adjusted to obtain the desired conversion into monoester, in a preferred manner to obtain the conversion of 50% of the diol encompassed in said diol feedstock, preferably 60% of the diol, and very preferably 70% of the diol.

Said reactive distillation column is then fed with said pre-esterified diol feedstock and with the fraction of said carboxylic acid feedstock that does not feed said pre-esterification section.

Water Elimination Step

In accordance with the invention, the method for esterification of a diol feedstock according to the invention comprises at least one step for eliminating the water produced by the esterification reaction.

In one embodiment of the invention, said water elimination step comprises at least one heterogeneous azeotropic distillation section, decoupled from the esterification step, comprising at least two distillation columns for heterogeneous azeotropic distillation and a decanter. Said distillate that comprises water produced by said esterification step feeds a first distillation column, in which a driver is present. The driver forms an azeotrope with water, which is drawn off at the top of said first distillation column, which thus produces a carboxylic acid residue at the bottom. The water/driver azeotrope that is drawn off at the top of said first distillation column is condensed in a decanter tank. Because of the low miscibility between the driver and water, a phase separation takes place: a water-rich phase that is sent back as reflux into the second distillation column and a driver-rich phase that is sent back as reflux into the first distillation column producing the carboxylic acid residue are obtained. Preferably, the carboxylic acid that is entrained in the distillate of the first distillation column is preferably shared in the driver-rich phase and is therefore sent back into the first distillation column. The second distillation column produces a water residue, which is eliminated by the method, at the bottom, and a distillate consisting of the water/driver azeotrope, which is condensed in the decanter tank, at the top.

In this embodiment of the invention, said water elimination step can also advantageously comprise a liquid-liquid extraction section located upstream from said first distillation column for heterogeneous azeotropic distillation. Said distillate that is produced by said esterification step feeds at the top said liquid-liquid extraction section, which is fed at the bottom with the driver. Said liquid-liquid extraction section produces at the top an extract that feeds said first distillation column for heterogeneous azeotropic distillation and at the bottom a raffinate that feeds said second heterogeneous azeotropic distillation column.

The driver that is used in said water elimination step is an ether such as diethyl ether, methyl tert-butyl ether, diisopropyl ether, an ester such as methyl acetate, ethyl acetate, isopropyl acetate, a ketone such as MEK, or a hydrocarbon such as hexane, cyclohexane, or benzene. In a very preferred manner, said driver is MEK. In the case where MEK is used as a driver, it is advantageously possible to use the MEK by-product that is generated in the esterification step and in the pyrolysis step.

In another embodiment of the invention, said water elimination step is coupled to said esterification step. Coupled is defined as that the first heterogeneous azeotropic distillation column is common with the reactive distillation column of said esterification step. In this embodiment of the invention, the addition of the driver is fed directly into said esterification step, in the condenser of the reactive distillation column. Because of the presence of the driver, a separation takes place in the condenser of the reactive distillation column between a driver-rich phase and a water-rich phase. The driver-rich phase is sent back as reflux into the reactive distillation column. The water-rich phase is sent to a distillation column, which produces a water residue at the bottom and vapors that are sent to the condenser of said reactive distillation column at the top.

The carboxylic acid that is entrained at the top of said reactive distillation column and condensed in the condenser is preferably shared in the driver-rich phase and is therefore sent back into said reactive distillation column. In this embodiment, the driver is to be stable under the operating conditions of the reactive distillation column, in particular in the presence of heterogeneous catalyst and water. The driver that is used in this embodiment is an ether such as diethyl ether, methyl tert-butyl ether, diisopropyl ether, a ketone such as MEK, or a hydrocarbon such as hexane, cyclohexane, or benzene. In a very preferred manner, said driver is MEK. In the case where MEK is used as a driver, it is advantageously possible to use the MEK by-product that is generated in the esterification step and in the pyrolysis step. In this case, the carboxylic acid to diol molar ratio at the inlet of the esterification step is preferably between 2 and 2.5.

Optional Pyrolysis Step

The conversion method according to the invention advantageously comprises a pyrolysis step that comprises a pyrolysis reactor fed with said diol-diester residue that is obtained from the esterification step, operated at a temperature of between 500 and 650° C. in such a way as to produce a pyrolysis effluent, with said pyrolysis step also comprising at least one separation section in which said pyrolysis effluent is cooled to a temperature of less than 100° C. in such a way as to produce at least one liquid pyrolysis effluent, which is advantageously recycled into the esterification step in a mixture with the carboxylic acid feedstock, and a vapor pyrolysis effluent.

The pyrolysis reaction primarily transforms 1 mol of diol diester into 1 mol of diolefin and thus releases 2 mol of carboxylic acid. Primarily is defined as that more than 70 mol % of diester is converted into diolefin. Preferably more than 80 mol % of diester is converted into diolefin. Said pyrolysis reactor, called pyrolysis furnace, is operated at a temperature of between 500 and 650° C., preferably between 550 and 600° C., and in a preferred manner between 575 and 585° C. The optimal contact time within the pyrolysis furnace is based on the partial pressure of the diol diester injected into the pyrolysis furnace. It is typically 1 second for a diol-diester partial pressure of 0.1 MPa and 7 seconds for a diol-diester partial pressure of 0.04 MPa.

The effluent that is obtained from said pyrolysis reactor is quickly cooled to a temperature of less than 100° C., preferably less than 50° C., in such a way as to limit the formation of degradation products, for example by Diels-Alder reaction of diolefins on themselves. By way of illustration, in the case where the diolefin is 1,3-butadiene, such a degradation product is vinyl cyclohexene. The cooling of the effluent generates a liquid phase and a vapor phase that can be easily separated within a gas-liquid separator tank into a liquid pyrolysis effluent and a vapor pyrolysis effluent.

Said vapor pyrolysis effluent comprises more than 90% by weight, preferably more than 95% by weight, of diolefins (without considering the possible inert diluent used to reduce the diol-diester partial pressure within the pyrolysis furnace). Said vapor pyrolysis effluent can also contain light organic compounds, obtained from the pyrolysis of carboxylic acid, such as, for example, in the case where the carboxylic acid is acetic acid, methane, carbon monoxide, carbon dioxide, ketene, hydrogen, or else ethane. Said vapor pyrolysis effluent can be compressed and/or cooled in such a way as to condense the diolefins. The non-condensable organic compounds that are obtained from the pyrolysis of the carboxylic acid are thus eliminated at the top of a gas-liquid separator in the form of a light compound effluent. The diolefins, which are recovered at the bottom of the column, can then undergo one or more final purification steps that are well known to one skilled in the art. It is possible to cite in a non-limiting manner the purification on a sieve or on a clay. This makes it possible to eliminate the impurities and to obtain a diolefin effluent, which comprises more than 99%, in a preferred manner more than 99.5%, of diolefins.

Said liquid pyrolysis effluent consists for the most part of carboxylic acid. For the most part is defined as at least 50% by weight, and preferably at least 70% by weight. It also comprises other organic compounds such as, for example, diol diester that is not converted, intermediate pyrolysis compounds such as methyl vinyl carbinol acetate (MVCA), methyl ethyl ketone enol acetate (MEKEA), and crotyl acetate (CA), and by-products such as vinyl cyclohexene, methyl ethyl ketone (MEK) or methylacetylacetone (MAA), in the case where the carboxylic acid is acetic acid and the diol is 2,3-butanediol.

Among the intermediate pyrolysis compounds (i.e., the diester molecules that have lost one carboxylic acid fragment of the two necessary for the formation of diolefin), some of these compounds make it possible to increase the overall diolefin yield of the unit if they are recycled into the pyrolysis step, while others do not. By way of illustration, in the case where the carboxylic acid is acetic acid, and the diol is 2,3-butanediol, methyl vinyl carbinol acetate (MVCA) and crotyl acetate (CA) make it possible to increase the butadiene yield if they are recycled into the pyrolysis step, whereas this is not the case with methyl ethyl ketone enol acetate (MEKEA).

Now, these intermediate pyrolysis compounds are isomers, and therefore have physico-chemical properties that are very close. Furthermore, these intermediate pyrolysis compounds are heavily diluted in carboxylic acid. It turns out that when the diol feedstock is butanediol, regardless of the carboxylic acid in question, the relative volatility between carboxylic acid and the intermediate pyrolysis compounds is very close to one. All of these elements make the extraction of the intermediate pyrolysis compounds within the liquid pyrolysis effluent very difficult.

The liquid pyrolysis effluent is advantageously recycled to the esterification step in a mixture with the carboxylic acid feedstock.

Surprisingly enough, the use of the liquid pyrolysis effluent for constituting a portion of the carboxylic acid feedstock of the esterification step does not degrade the performances of the esterification of diol and offers several unexpected advantages.

First of all, it is not necessary to separate the diester that is present in the liquid pyrolysis effluent from other compounds. Actually, during its recycling to the esterification step, the liquid pyrolysis effluent is introduced onto an intermediate plate located between the mixed zone and the lower separation zone, in a mixture with the carboxylic acid feedstock. The diester then falls directly to the bottom of the reactive distillation column with the diester that is freshly produced in the reactive distillation column. The recycling of the liquid pyrolysis effluent therefore makes it possible to eliminate a distillation column for separating the diester that is not converted from the other components of the liquid pyrolysis effluent and the associated operating costs (evaporation of approximately 80% by weight of the liquid pyrolysis effluent, primarily consisting of carboxylic acid).

In addition, in the case where the diol is 2,3-butanediol and the carboxylic acid is acetic acid, within the reactive distillation column described above, the MEKEA intermediate pyrolysis compound and the MAA by-products are hydrolyzed to form MEK, while the other intermediate pyrolysis compounds such as methyl vinyl carbinol acetate (MVCA) and crotyl acetate (CA) are not converted or are sparingly converted. This difference in reactivity between the intermediate pyrolysis compounds is particularly advantageous because MEKEA—which would not have produced butadiene if it was recycled in the pyrolysis furnace—can thus be easily separated from the other intermediate pyrolysis compounds that are methyl vinyl carbinol acetate (MVCA) and crotyl acetate (CA)—that produce butadiene if they are recycled in the pyrolysis furnace. Furthermore, the hydrolysis of 1 mol of MAA by-product releases 1 mol of acetic acid, which makes it possible to limit the additions of acetic acid during the process.

Finally, another unexpected effect is associated with the production of MEK within the reactive distillation column, starting from by-products or intermediate pyrolysis compounds that cannot be upgraded. In the esterification method according to the invention, the acetic acid/diol molar ratio has been greatly decreased in relation to that of the esterification method of the prior art. A direct consequence is that the distillate that is drawn off at the top of the reactive distillation column is much more rich in water and therefore much less rich in acetic acid. Actually, for an initial carboxylic acid/diol molar ratio that is less than 2.5, which is equivalent to having a final water/AA molar ratio that is greater than 4, the distillate that is obtained at the top of the water/acetic acid/MEK column is two-phase. The MEK that is thus produced within the reactive distillation column plays the role of driver to separate the water and the acetic acid. It is therefore seen that the direct recycling of the liquid pyrolysis effluent in the esterification step makes it possible to upgrade certain by-products and intermediate pyrolysis compounds (which cannot be upgraded into butadiene) to form in situ the driver that is necessary to the separation of the water and the acetic acid. This unexpected effect makes it possible to eliminate the purchase of additions of driver within the esterification method.

DESCRIPTION OF THE FIGURES

Figure 1:
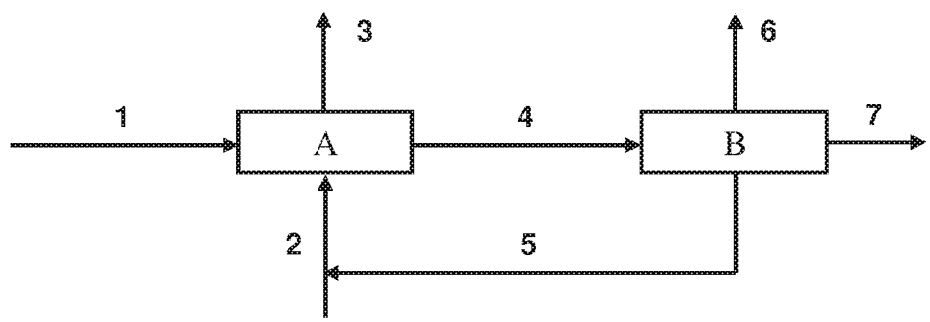
FIG. 1 present a possible overall arrangement of the method according to the invention.

FIG. 1 presents a possible overall arrangement of the method according to the invention. A diol feedstock (1) and a carboxylic acid feedstock (2) feed, in an esterification step (A), a reaction-separation section in which the diol [is] converted into diol diester. The distillate comprising water (3) is eliminated from the method, and the diol-diester residue (4) feeds a pyrolysis step (B). Said pyrolysis step (B), which comprises a pyrolysis reactor and at least one separation section, produces a liquid pyrolysis effluent (5), which is recycled into the esterification step (A), an effluent consisting of light compounds (6), and a diolefin effluent (7) that constitutes the main product of the method according to the invention, when the pyrolysis step is present in the method. Another main product is diol diester.

Figure 2:
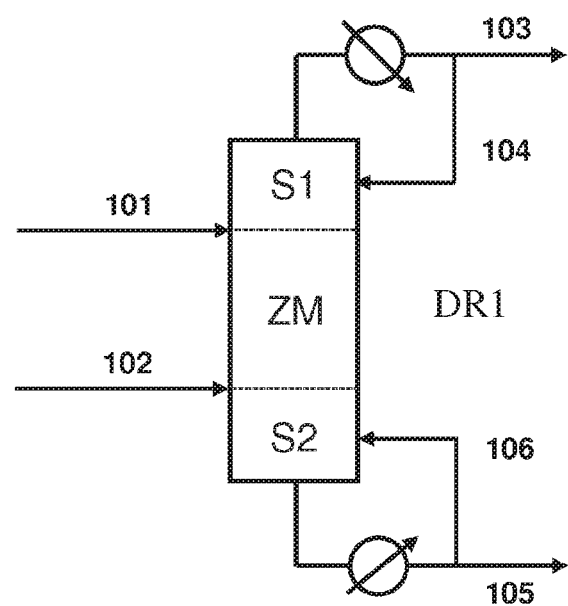
FIG. 2 presents a reactive distillation column (DR1) according to a first variant of the invention.

FIG. 2 presents a reactive distillation column (DR1) according to a first variant of the invention, which makes it possible to carry out the esterification step. The alcohol feedstock (101) is introduced above the mixed reaction-separation zone of the column (DR1), whereas the carboxylic acid feedstock (102) is introduced below this mixed reaction-separation zone. The mixed zone is framed by two separation sections (S1) and (S2), respectively at the top and at the bottom of the column (DR1). At the top of the column (DR1), the distillate comprising water (103) is an effluent that consists essentially of water and carboxylic acid. A portion of this distillate (104) is sent back as reflux into the area of the plate at the top of the column (DR1). A diol-diester residue (105) that consists for the most part of diol diester is recovered at the bottom of the column. A portion of this residue (106) is sent back as reboiling into the area of the plate at the bottom of the column (DR1).

Figure 3:
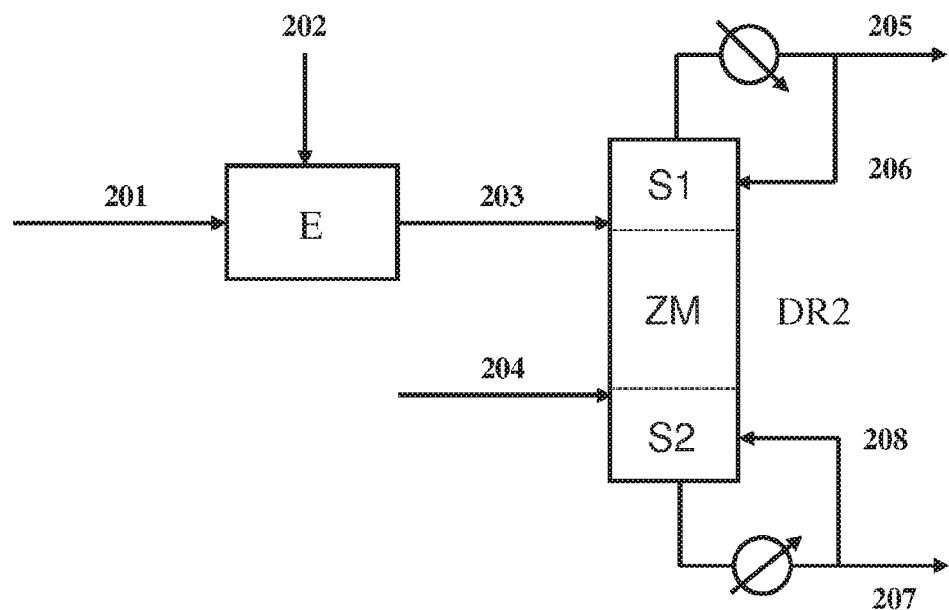
FIG. 3 presents another variant of the invention, in which the etherification step comprises a column (DR2) which is preceded by a pre-esterification section (E).

FIG. 3 presents another variant of the invention, in which the esterification step comprises a column (DR2) preceded by a pre-esterification section (E). The diol feedstock (201) and a fraction of the carboxylic acid feedstock (202) are introduced into the pre-esterification reactor (E). A pre-esterified diol feedstock (203) consisting of diol diester, diol monoester, diol, water, and carboxylic acid results. This feedstock is introduced between the upper separation zone (S1) and the mixed reaction/separation zone (ZM) of the column (DR2). The remaining fraction of the carboxylic acid feedstock (204) is introduced between the mixed reaction/separation zone (ZM) and the lower separation zone (S2) of the column (DR2). At the top of the column, the distillate comprising water (205) is an effluent that consists essentially of water and acetic acid. A portion of this distillate (206) is sent back as reflux into the area of the plate at the top of the column (DR2). A diol-diester residue that consists for the most part of diol diester is recovered at the bottom of the column (207). A portion of this residue (208) is sent back as reboiling into the area of the plate at the bottom of the column (DR2).

EXAMPLE 1—ESTERIFICATION IMPLEMENTED BY REACTIVE DISTILLATION (FOR COMPARISON)

This example shows the performances of a method for esterification by reactive distillation implemented according to the teaching of the prior art.

The esterification of 2,3-butanediol (2,3-BDO) by acetic acid is catalyzed by sulfuric acid. This esterification is implemented in a reactive distillation under the operating conditions described in "Continuous Process for Acetylation of 2,3-Butylene Glycol," Industrial and Engineering Chemistry, 1945, Vol. 37, No. 9, pp. 872-877.

The reactive distillation column comprises 13 plates numbered from top to bottom. 50.46 kmol/h of feedstock at 110° C., comprising 2,3-BDO and 1% by mass of sulfuric acid in relation to 2,3-BDO, is introduced in the area of the plate 3. 300 kmol/h of acetic acid at 110° C. is injected at the bottom of the column (plate 13). The distillate reflux is reinjected at plate 1, with a molar reflux rate of 1, and the residue reflux is reinjected at plate 13, with a molar reboil rate of 5.3.

The column is operated with a pressure and a temperature at the top of 0.1 MPa and 103.5° C., and a pressure and a temperature at the bottom of 0.11 MPa and 149.9° C.

The dwell time in the column is 2 hours. The dwell time per plate is 9.23 minutes (with the homogeneous catalyst being distributed throughout the column, it is assumed that the dwell time is distributed equally over all of the plates).

The acetic acid/2,3-BDO molar ratio in the column is 6.

Under these conditions, the column produces 259.8 kmol/h of distillate and 90.66 kmol/h of residue.

2,3-BDO diester with a purity of 99.9 mol % (diester flow rate in the residue/flow rate of diol+monoester+diol in the residue) is obtained, with a 2,3-BDO diester yield of 99.2 mol % (diester flow rate in the residue/flow rate of diol at the inlet).

The losses in diol, monoester and diester, in the distillate are 0.7% (flow rates of diol+monoester+diester in the distillate/diol flow rate at the inlet).

It is possible to note that in the method according to the prior art, the addition of a large excess of acid at the bottom of the column makes it possible to maintain the temperature at around 150° C., for the purpose of limiting the reactions for degradation of 2,3-butanediol into MEK. The addition of this large excess of acetic acid has two negative consequences:
  A significant circulation of acetic acid during the process
  The necessity of separating the diester from acetic acid, after the homogeneous catalyst is eliminated under vacuum.

EXAMPLE 2—ESTERIFICATION IMPLEMENTED BY REACTIVE DISTILLATION (INVENTION)

This example shows the performances of a method for esterification by reactive distillation implemented according to the invention.

The reactive distillation column comprises 20 plates numbered from top to bottom. 50 kmol/h of feedstock, consisting of 2,3-BDO at 110° C., is introduced in the area of the plate 5. 150 kmol/h of acetic acid at 110° C. is injected in the area of the plate 15. The distillate reflux is reinjected at plate 1, with a molar reflux rate of 1, and the residue reflux is reinjected at plate 20, with a molar reboil rate of 5.3.

The column is operated with a pressure and a temperature at the top of 0.1 MPa and 90.9° C., and a pressure and a temperature at the bottom of 0.11 MPa and 206.3° C.

The dwell time in the column is 2 hours. The dwell time per reactive plate is 24 minutes. The column comprises 5 reactive plates containing an ion-exchange acid resin (Dry Amberlyst 35), with these plates being numbered 6, 8, 10, 12 and 14.

The acetic acid/2,3-BDO molar ratio in the column is 3.

Under these conditions, the column produces 150.0 kmol/h of distillate and 50.0 kmol/h of residue.

2,3-BDO diester with a purity of 99.3 mol % (diester flow rate in the residue/flow rate of diol+monoester+diol in the residue) is obtained, with a 2,3-BDO diester yield of 99.3 mol % (diester flow rate in the residue/flow rate of diol at the inlet).

The losses in diol, monoester and diester, in the distillate are 0.4 mol % (flow rates of diol+monoester+diester in the distillate/diol flow rate at the inlet).

The method according to the invention makes it possible to reduce considerably the acetic acid flow rate in relation to the 2,3-butanediol flow rate without significantly reducing the performance of the reactive distillation (purity of 99.3 mol % according to the invention versus 99.9 mol % according to the prior art; yield of 99.3 mol % according to the invention versus 99.2 mol % according to the prior art). The temperature within the column used in the method according to the invention increases significantly only at the bottom of the column, in the zone consisting only of separation stages (plates 15 to 20) that makes it possible to carry out the separation between the diol/monoester/diester radicals, on the one hand, and acetic acid/water, on the other hand. With the catalyst being located above this zone, where the temperature does not exceed 135° C., the reactions for degradation of 2,3-butanediol into MEK are very significantly limited.

EXAMPLE 3—RECYCLING OF THE LIQUID PYROLYSIS EFFLUENT

This example shows the possibility of recycling the liquid pyrolysis effluent according to the invention.

The residue of Example 2 feeds a pyrolysis step, which comprises a pyrolysis furnace operated at 580° C. with a contact time of approximately 2 s. The pyrolysis effluent is quickly cooled to 45° C. and condenses into a liquid pyrolysis effluent. The uncondensed part, which constitutes the vapor pyrolysis effluent, comprises 97.5% by weight of 1,3-butadiene. The composition of the liquid pyrolysis effluent is indicated in Table 1.

TABLE 1

Composition by Mass and Molar Composition of the Liquid Pyrolysis Effluent.

|  | % by Mass | Mol % |
|---|---|---|
| AA | 79.60% | 83.54% |
| 2,3-BDOdiAc | 2.81% | 1.02% |
| BDE | 9.01% | 10.51% |
| VCH | 0.62% | 0.36% |
| MEK | 0.57% | 0.50% |
| MVCA | 0.95% | 0.52% |
| MEKEA | 3.49% | 1.93% |
| CA | 2.64% | 1.46% |
| MAA | 0.31% | 0.17% |

2,3-BDODiAc = 2,3-Butanediol Diacetate, BDE = Butadiene, VCH = Vinyl Cyclohexene, MEK = Methyl Ethyl Ketone, MAA = Methylacetylacetone, MVCA = Methyl Vinyl Carbinol Acetate, MEKEA = Methyl Ethyl Ketone Enol Acetate, CA = Crotyl Acetate.

Two tests for esterification of 2,3-butanediol by acetic acid were carried out. One test was carried out with pure acetic acid, and the other was carried out with the liquid pyrolysis effluent described above. These tests were conducted in a batch reactor with a volume of 30 mL at atmospheric pressure, equipped with a condenser. The temperature is constant and regulated at 110° C. owing to a coolant in a double jacket. The reactions are carried out in the presence of an ion-exchange resin (Dry Amberlyst 35) present at a concentration of 2.2 mol % in relation to the 2,3-butanediol. These reactions were carried out with an acetic acid/2,3-butanediol molar ratio of 6. These tests made it possible to monitor the kinetics of the esterification reaction, as well as the changes in the different impurities and intermediate pyrolysis compounds over time.

The comparison of the results of these two tests is presented in Table 2 below:

TABLE 2

Results of the Two Tests for Esterification of 2,3-BDO with Pure Acetic Acid and with a Liquid Pyrolysis Effluent

|  | Acetic Acid | Pyrolysis Liquid |
|---|---|---|
| Time (h) | 20 | 20 |
| $x_{AA}$ | 65.9% | 69.1% |
| $x_{H2O}$ | 20.1% | 15.6% |
| $x_{2,3\text{-}BDO}$ | 0.8% | 0.7% |
| $x_{2,3\text{-}BDOmonoAc}$ | 6.1% | 6.2% |
| $x_{2,3\text{-}BDOdiAc}$ | 7.1% | 8.5% |
| $k_1$ (L · mol$^{-1}$ · h$^{-1}$) | 0.0500 | 0.0500 |
| $k_{-1}$ (L · mol$^{-1}$ · h$^{-1}$) | 0.0217 | 0.0238 |
| $k_2$ (L · mol$^{-1}$ · h$^{-1}$) | 0.0200 | 0.0200 |
| $k_{-2}$ (L · mol$^{-1}$ · h$^{-1}$) | 0.0571 | 0.0645 |
| $K_1 = k_1/k_{-1}$ | 2.3 | 2.1 |
| $K_2 = k_2/k_{-2}$ | 0.35 | 0.31 |
|  | $C^{initial}$ (mol · L$^{-1}$) | $C^{final}$ (mol · L$^{-1}$) |
| BDE | — | 1.2551 0.3256 |
| VCH | — | 0.0864 0.0542 |
| MEK | — | 0.0794 0.6371 |
| MVCA | — | 0.1323 0.1407 |
| MEKEA | — | 0.4862 0.0117 |
| CA | — | 0.3678 0.2905 |
| MAA | — | 0.0432 0.0000 |

With AA=acetic acid, 2,3-BDO=2,3-BDO, 2,3-BDOmonoAc=2,3-butanediol monoester, 2,3-BDOdiAc=2,3-butanediol diester, and:

$k_1$=kinetic constant of the reaction for esterification of diol into monoester
$k_1$=kinetic constant of the reaction for hydrolysis of monoester into diol
$k_2$=kinetic constant of the reaction for esterification of monoester into diester
$k_2$=kinetic constant of the reaction for hydrolysis of diester into monoester
$K_1$=thermodynamic constant of the reaction for esterification of diol into monoester
$K_2$=thermodynamic constant of the reaction for esterification of monoester into diester It can be noted that the esterification kinetics and the thermodynamic equilibriums remain almost unaffected by the use of the liquid pyrolysis effluent that is obtained by pyrolysis of the 2,3-butanediol diester. Relative to the impurities that are present in the liquid pyrolysis effluent, some have changed over time. The concentration of butadiene was almost divided by 4 between the beginning of the reaction and the end; this is explained by its low boiling point of −4.4° C. at atmospheric pressure: butadiene was not condensed by the refrigerant topping the batch reactor and was therefore lost. With the concentrations of VCH and MVCA being relatively low, it is possible to state that these concentrations did not change much, with deviations of −37.3% and +6.3%, respectively. The CA, initially in a larger quantity, also does not change significantly during the reaction (−21.0%). In contrast, it is shown here that MEKEA (−97.6%) and MAA (−100%) disappear almost totally during the reaction to provide MEK. Actually, the disappearance of MEKEA and MAA corresponds to 0.5176 mol·$L^{-1}$, and the formation of MEK corresponds to 0.5577 mol·$L^{-1}$.

It is thus demonstrated that it is possible to use the liquid pyrolysis effluent directly in the step for esterification of 2,3-BDO. The intermediate compounds that can lead to butadiene by recycling in the pyrolysis furnace (MVCA, CA) are little impacted under the test conditions, whereas the intermediate MEKEA compounds that can provide MEK by recycling in the pyrolysis furnace and the MAA by-product are converted into MEK.

The invention claimed is:

1. A conversion method that is fed with a diol feedstock that comprises at least 90% by weight of diol and a carboxylic acid feedstock that comprises at least 80% by weight of carboxylic acid, with said method comprising at least:
    esterification fed with at least said diol feedstock and at least said carboxylic acid feedstock, having feed flow rates adjusted in such a way that the esterification has a carboxylic acid/diol molar ratio at the inlet of said esterification between 2 and 4, with said esterification comprising at least one reactive distillation in a reactive distillation column operated at a temperature of between 40 and 280° C., at a pressure of between 0.01 and 0.5 MPa, with a molar reflux rate of between 0.5 and 10, and a molar reboil rate of between 0.5 and 10, said column having a mixed reaction/separation zone located between two separation zones, with each of said separation zones having an effectiveness of at least two theoretical stages, said mixed zone comprising an acidic heterogeneous catalyst, said esterification producing at least one distillate that comprises water and a diol-diester residue; and
    water elimination fed with said distillate comprising water to produce at least one water effluent.

2. The conversion method according to claim 1, in which the reactive distillation column has a dwell time, defined as the volume of the reactive distillation column divided by the volumetric flow rate of said diol feedstock and said carboxylic acid feedstock, between 0.5 h and 10 h.

3. The conversion method according to claim 1, in which said water elimination comprises heterogeneous azeotropic distillation in the presence of a driver comprising:
    a first heterogeneous azeotropic distillation in a first column that is fed with said distillate that comprises water and to produce a distillate that comprises a water/driver azeotrope and a carboxylic acid residue;
    decanting in a decanter that is fed with said distillate that comprises the water/driver azeotrope to produce a water-rich phase and a driver-rich phase, with said driver-rich phase being recycled as reflux to said first heterogeneous azeotropic distillation; and
    a second heterogeneous azeotropic distillation in a second column that is fed with said water-rich phase, which produces a distillate that is recycled to said decanter and a water residue.

4. The conversion method according to claim 1, in which said water elimination comprises:
    liquid-liquid extraction in a section that is fed at the top with said distillate that comprises water and at the bottom with a driver and that produces an extract at the top and a raffinate at the bottom;
    a first heterogeneous azeotropic distillation in a first column that is fed with said extract and that produces a distillate that comprises a water/driver azeotrope and a carboxylic acid residue;
    a second heterogeneous azeotropic distillation in a second column that is fed with said raffinate and that produces a distillate that comprises a water/driver azeotrope and a water residue; and
    decanting in a decanter that is fed with said distillate that comprises the water/driver azeotrope that is obtained from said first heterogeneous azeotropic distillation and with said distillate that comprises the water/driver azeotrope that is obtained from said second heterogeneous azeotropic distillation to produce a water-rich phase and a driver-rich phase, with said driver-rich phase being recycled as reflux to said first column and said water-rich phase being recycled as reflux to said second column.

5. The conversion method according to claim 1, in which said esterification and said water elimination are coupled, with said esterification also being fed with a driver, which brings about a separation between a water-rich phase and a driver-rich phase in a condenser of said reactive distillation column, with said water-rich phase being removed to produce the distillate comprising water and feeding said distillate comprising water to a distillation column that produces a water residue and a distillate, wherein said distillate is recycled to said condenser of said reactive distillation column, with said driver being an ether, a ketone, or a hydrocarbon.

6. The conversion method according to claim 1, also comprising:
    pyrolysis of the diol-diester residue from said esterification at a temperature of between 500 and 600° C. in a reactor to produce a pyrolysis effluent; and
    at least one separation in a section in which said pyrolysis effluent is cooled to a temperature that is lower than 100° C. in such a way as to produce at least one liquid pyrolysis effluent and a vapor pyrolysis effluent, with the vapor pyrolysis effluent being separated into a light compound effluent and a diolefin effluent.

7. The conversion method according to claim 6, in which said liquid pyrolysis effluent is mixed with said carboxylic acid feedstock that feeds said conversion method.

8. The conversion method according to claim 1, in which said diol is a butanediol, a pentanediol, or a hexanediol.

9. The conversion method according to claim 1, in which said diol is 2,3-butanediol, 1,3-butanediol, or 1,4-butanediol.

10. The conversion method according to claim 1, said esterification further comprising a pre-esterification step in a section operating with a fixed bed of a heterogeneous acid catalyst, said pre-esterification being operated at a pressure of between 0.01 and 0.5 MPa, and at a temperature of between 80° C. and 170° C., and said section being fed with said diol feedstock and a fraction of said carboxylic acid feedstock and producing a pre-esterified diol feedstock, which is then fed to the esterification with the rest of the carboxylic acid feedstock.

11. The conversion method according to claim 1, in which said carboxylic acid is an aliphatic carboxylic acid.

12. The conversion method according to claim 11, in which said aliphatic carboxylic acid is formic acid, acetic acid, propanoic acid, or butanoic acid.

13. The conversion method according to claim 3, wherein the driver is an ether, ester, ketone or hydrocarbon.

14. The conversion method according to claim 4, wherein the driver is an ether, ester, ketone or hydrocarbon.

15. The conversion method according to claim 14, in which said driver is methylethylketone.

16. The conversion method according to claim 13, in which said driver is methylethylketone.

* * * * *